(12) United States Patent
Fraone et al.

(10) Patent No.: US 10,588,639 B2
(45) Date of Patent: Mar. 17, 2020

(54) SPRING-FIT SURGICAL GUIDES

(71) Applicant: ConforMIS, Inc., Bedford, MA (US)

(72) Inventors: Steve Fraone, Brighton, MA (US); Scott Doody, Melrose, MA (US); Paul Dietz, Charlestown, MA (US); Martin J. Polinski, Wrentham, MA (US); Raymond A. Bojarski, Attleboro, MA (US)

(73) Assignee: ConforMIS, Inc., Billerica, MA (US)

( * ) Notice: Subject to any disclaimer, the term of this patent is extended or adjusted under 35 U.S.C. 154(b) by 383 days.

(21) Appl. No.: 15/113,304

(22) PCT Filed: Jan. 21, 2015

(86) PCT No.: PCT/US2015/012199
§ 371 (c)(1),
(2) Date: Jul. 21, 2016

(87) PCT Pub. No.: WO2015/112566
PCT Pub. Date: Jul. 30, 2015

(65) Prior Publication Data
US 2017/0027587 A1    Feb. 2, 2017

Related U.S. Application Data

(60) Provisional application No. 61/930,873, filed on Jan. 23, 2014.

(51) Int. Cl.
*A61B 17/15* (2006.01)
*A61B 17/17* (2006.01)
*A61B 17/00* (2006.01)

(52) U.S. Cl.
CPC ............ *A61B 17/15* (2013.01); *A61B 17/155* (2013.01); *A61B 17/157* (2013.01); *A61B 17/1764* (2013.01); *A61B 17/1739* (2013.01); *A61B 17/1742* (2013.01); *A61B 17/1778* (2016.11);
(Continued)

(58) Field of Classification Search
CPC ...... A61B 17/15; A61B 17/157; A61B 17/155
See application file for complete search history.

(56) References Cited

U.S. PATENT DOCUMENTS 4,241,634 A * 12/1980 Ambler .................... B27G 5/02
                                                                  83/522.25
4,658,875 A *  4/1987 Grabovac .............. B27G 13/04
                                                                  144/117.1
(Continued)

FOREIGN PATENT DOCUMENTS

WO  WO 2004/017842 A2   3/2004  ............. A61B 17/15
WO  WO 2013/030370 A1   3/2013  ............. A61B 17/17
WO  WO 2015/112566 A1   7/2015  ............. A61B 17/15

OTHER PUBLICATIONS

International Searching Authority, International Search Report—International Application No. PCT/US15/12199 dated Apr. 9, 2015, together with the Written Opinion from the International Searching Authority, 19 pages.

*Primary Examiner* — David W Bates
(74) *Attorney, Agent, or Firm* — Sunstein Kann Murphy & Timbers LLP

(57) ABSTRACT

Various embodiments of devices, systems, and methods for surgical procedures, including spring-fit guides for improved guidance of surgical instruments, are disclosed.

13 Claims, 7 Drawing Sheets

(52) U.S. Cl.
CPC . *A61B 17/1782* (2016.11); *A61B 2017/00526* (2013.01)

(56) References Cited

U.S. PATENT DOCUMENTS

| | | | | |
|---|---|---|---|---|
| 4,738,253 | A * | 4/1988 | Buechel | A61B 17/157 606/80 |
| 5,261,895 | A | 11/1993 | Kablik | 604/249 |
| 5,437,677 | A | 8/1995 | Shearer et al. | 606/96 |
| 6,113,618 | A | 9/2000 | Nic | 606/176 |
| 6,395,004 | B1 | 5/2002 | Dye et al. | 606/86 |
| 8,900,242 | B2 * | 12/2014 | Murray | A61B 17/157 606/88 |
| 9,743,940 | B2 * | 8/2017 | Catanzarite | A61B 17/157 |
| 2004/0249385 | A1 * | 12/2004 | Faoro | A61B 17/157 606/88 |
| 2005/0049603 | A1 * | 3/2005 | Calton | A61B 17/155 606/87 |
| 2005/0187635 | A1 | 8/2005 | Metzger | 623/20.15 |
| 2006/0293681 | A1 * | 12/2006 | Claypool | A61B 17/155 606/87 |
| 2012/0253350 | A1 * | 10/2012 | Anthony | A61B 17/14 606/87 |
| 2013/0325018 | A1 | 12/2013 | Thomas et al. | 606/88 |

\* cited by examiner

SPRING-FIT SURGICAL GUIDES

RELATED APPLICATIONS

This application claims the benefit of U.S. Provisional Application No. 61/930,873, entitled "Spring-Fit Surgical Guides" and filed Jan. 23, 2014, the disclosure of which is incorporated herein by reference in its entirety

FIELD

The present teachings generally relate to surgical repair systems (e.g., resection cut strategy, guide tools, and implant components) as described in, for example, U.S. patent application Ser. No. 13/397,457, entitled "Patient-Adapted and Improved Orthopedic Implants, Designs And Related Tools," filed Feb. 15, 2012, and published as U.S. Patent Publication No. 2012-0209394, which is incorporated herein by reference in its entirety. In particular, the present teachings provide surgical tools, systems, methods, and techniques incorporating features to facilitate preparation of a patient's anatomical surfaces for installation of implant components.

BACKGROUND

The natural anatomical joint structures of an individual may undergo degenerative changes due to a variety of reasons, including injury, osteoarthritis, rheumatoid arthritis, or post-traumatic arthritis. When such damage or degenerative changes become far advanced and/or irreversible, it may ultimately become necessary to replace all or a portion of the native joint structures with prosthetic joint components. Joint replacement is a well-tolerated surgical procedure that can help relieve pain and restore function in injured and/or severely diseased joints, and a wide variety of prosthetic joints are well known in the art, with different types and shapes of joint replacement components commercially available to treat a wide variety of joint conditions.

As part of the surgical repair procedure, the underlying anatomical support structures are typically prepared to receive the joint implant components. For example, the placement of a femoral implant component can typically involve preparation of the caudad portion of the femoral bone (otherwise known as the distal head of the femur). This may include surgical resection (e.g., cutting, drilling, rongeuring, scraping) of portions of the medial and/or lateral condyles of the femur, as well as the resection of other anatomical features of the femur and/or surrounding soft tissues. This preparation will desirably create an anatomical support structure capable of accommodating and adequately supporting the femoral implant component or components, which is ultimately secured to the femur. Similar surgical steps can be performed to the tibia and/or the patella, as well as other anatomical structures, as necessary.

One or more surgical guide tools or jigs can be used to assist the surgeon in preparing the underlying anatomical support structure(s). There is a need, however, for improved surgical guide tools and jigs to improve the accuracy, reproducibility, and/or ease of preparing underlying anatomical support structure(s) for an implant.

BRIEF DESCRIPTION OF THE DRAWINGS

FIG. 7b is a front view of the guide slot embodiment of FIG. 7a;

FIG. 8b is a front view of the guide slot embodiment of FIG. 8a;

DETAILED DESCRIPTION

Figure 1:
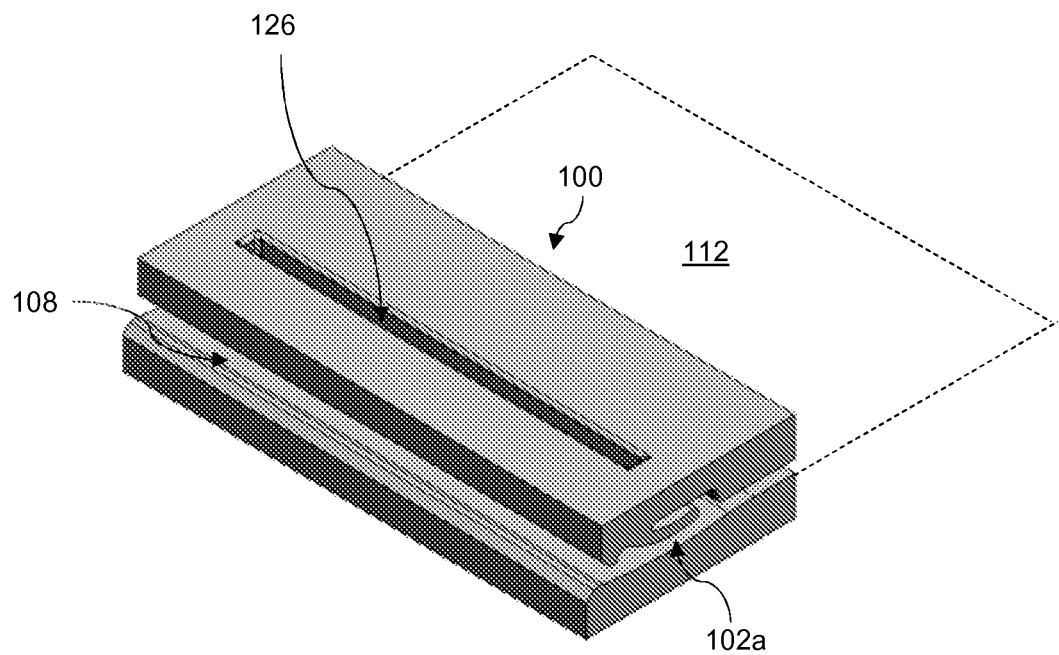
FIG. 1 is a perspective view of a first exemplary guide slot embodiment.

Reference will now be made in detail to the present embodiments (exemplary embodiments) of the invention, examples of which are illustrated in the accompanying drawings. Wherever possible, the same reference numbers will be used throughout the drawings to refer to the same or like parts. In this application, the use of the singular includes the plural unless specifically stated otherwise. Furthermore, the use of the term "including," as well as other forms, such as "includes" and "included," is not limiting. Also, terms such as "element" or "component" encompass both elements and components comprising one unit and elements and components that comprise more than one subunit, unless specifically stated otherwise. Also, the use of the term "portion" may include part of a moiety or the entire moiety. Any section headings used herein are for organizational purposes only and are not to be construed as limiting the subject matter described.

A variety of surgical guide tools can be used to assist surgeons in preparing a joint for an implant. Some surgical guide tools include guiding formations for receiving a surgical instrument and guiding it along a desired path or plane. Such guiding formations can comprise surfaces, slots, holes, apertures, shielding elements, stops (e.g., depth stops), and/or any other structures intended to direct and/or limit movement of a surgical instrument. Often, surgical guides are referred to as captured or uncaptured. A captured guide can be a guide that surrounds at least a portion of three or more sides of a surgical instrument. For example, a captured guide can comprise an aperture that can completely surround a portion of a guide tool. A captured guide can also comprise a slot having a U-shaped cross-section that can surround a portion of a surgical instrument on all but the open side. An uncaptured guide can comprise, for example, a single, exposed surface, along which a surgical instrument can be moved. The term "slot" will be used herein to generally identify a captured guide. Any of the slot embodiments described below can comprise one or more of various cross-sectional shapes (e.g., circular, square, rectangle, oblong, elliptical, U-shaped) and can be configured to receive one or more of various different types of surgical instruments (e.g., drill, saw, broach, pins, K-wires).

Typically, a guide slot has interior dimensions slightly oversized relative to the dimensions of the surgical instrument it is intended to receive. This may be done to, for example, ease insertion, accommodate manufacturing tolerances/variances/minimum-feature-sizes, and/or accommodate dimensional changes based on, for example, environmental factors and/or properties of the guide material. Such oversizing of guide slots can, however, have undesirable effects, such as, for example, permitting unintended lateral movement of the surgical instrument relative to the longitudinal axis of insertion of the instrument within the guide slot (e.g., skiving of a saw blade), deviation of the surgical instrument from a predetermined cutting plane, and/or other unintended movement of the surgical instrument, resulting in a reduction in accuracy of placement of the surgical instrument within the tissue of interest. In some cases, various of the undesirable effects described above associated with oversizing of slots can also be caused, at least in part, by inherent flexibility of the guide slot due to structural and/or material properties of the body of the slot.

As an example, currently, some surgical guides are manufactured using a selective laser sintering (SLS) process with a polymer powder material to produce a unitary surgical guide, including one or more guide slots, formed of nylon. In some cases, due to limitations of the SLS manufacturing process and/or inherent flexibility of the nylon body, guide slots with typical all-flat surfaces in such devices may allow for a certain amount of undesired movement (e.g., skiving of a saw blade) within the slot during use.

Various embodiments of surgical guides disclosed herein include a guide slot having a spring-fit structure, which can provide improved guidance of surgical instruments relative to a typical guide slot, as discussed above. Generally, a spring-fit structure, as disclosed herein, can include one or more guiding surfaces, which may be supported, at least in part, by one or more flexing or spring portions. As used herein, a "flexing" portion or structure can include one or more springs and/or may comprise a structure capable of flexing due to the inherent properties of the material forming the structure, or a portion thereof, and the shape/dimensions of the structure. The flexing portion can be configured to enable the guiding surface to engage a surgical instrument inserted into the slot and move in order to accommodate and/or form fit the surgical instrument. The flexing portions may also enable the guiding surface(s) to apply one or more forces to the surgical instrument in one or more direction(s) generally perpendicular to the direction of insertion of the instrument, and thereby improve desired engagement of the instrument with various guiding surfaces of the slot and/or provide resistance to deviations of the surgical instrument from a predetermined cutting plane.

As illustrated by the various embodiments described below, a variety of spring-fit structures can be utilized with a guide slot. Further, in some embodiments, a spring-fit structure may form a portion (e.g., a side wall) of the slot itself. Additionally or alternatively, a spring-fit structure may be added to a slot or positioned adjacent to a slot. In some embodiments, a spring-fit structure may be integrally formed with a corresponding guide slot (e.g., a spring-fit structure and a corresponding guide slot may be unitary, having been formed in the same manufacturing process, such as, for example, a printing run of a 3-D printing apparatus). In other embodiments, a spring-fit structure may be a modular component, which is configured to be joined with a guide slot. In various embodiments, a guide slot and a spring-fit structure and/or a guide slot including a spring-fit structure can be incorporated into the body of a surgical guide. In some embodiments, a guide slot and a spring-fit structure may be integrally formed with the body of a surgical guide (e.g., a guide slot, a spring-fit structure, and a body of a surgical guide may be unitary, having been formed in the same manufacturing process, such as, for example, a printing run of a 3-D printing apparatus). Alternatively, a guide slot and spring-fit structure can comprise one or more modular components that can be joined with the body of a surgical guide.

Figure 2:
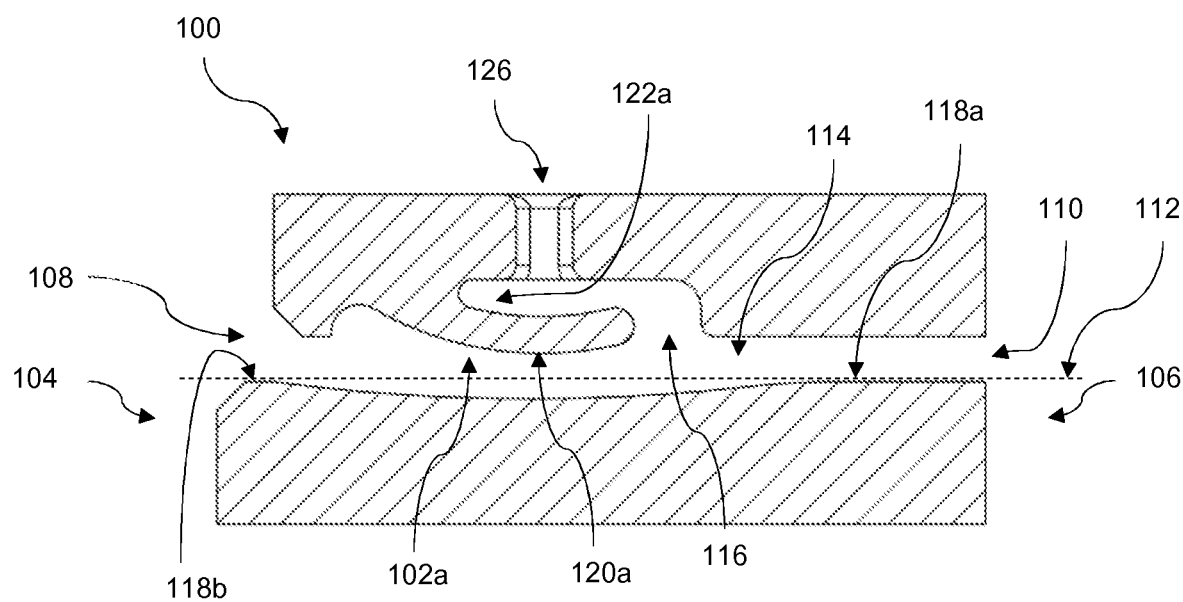
FIG. 2 is a cross-sectional view of the guide slot embodiment of FIG. 1 in a plane substantially perpendicular to entrance opening 108.

FIGS. 1 and 2 depict an exemplary embodiment of a guide slot 100 that includes a spring-fit structure 102a. In various embodiments, guide slot 100 can extend from the front side 104 to the rear side 106 of the body of a surgical guide. Slot 100 can receive a surgical instrument through entrance opening 108, and after passing through slot 100, the surgical instrument, or at least a portion of the surgical instrument, may exit slot 100 through exit opening 110, optionally, traveling substantially along predetermined cutting plane 112. Predetermined cutting plane 112 can be a specific plane along which the surgical guide and slot are designed to direct a surgical instrument into tissue to be cut. The boundaries of the interior of slot 100 may be defined, at least in part, by a cutting-plane side wall 114 and an opposing side wall 116, which is located substantially on the opposite side of the slot from cutting-plane side wall 114. One or more portions of cutting-plane side wall 114 (e.g., portion 118a, 188b, 118c) can be positioned and/or oriented substantially within the predetermined cutting plane 112. In various embodiments, the portions of the side wall within the predetermined cutting plane may comprise surfaces intended to contact and guide the surgical instrument, such that the surgical instrument ultimately travels substantially parallel thereto and thus along the predetermined cutting plane, as the instrument passes through the exit opening 110 of the slot 100 and into tissue to be cut. One or more spring-fit structures 102 (see, e.g., 102a) may be included, for example, in opposing side wall 116.

As mentioned above, the one or more spring-fit structures 102 can be configured to engage with and apply a force to the surgical instrument passing through slot 100. For example, spring-fit structure 102a can include a guide surface 120a and a flexing portion 122a, which supports guide surface 120a with respect to the body of the guide and can be substantially positioned between guide surface 120a and the body of the guide. Guide surface 120a can substantially face the cutting-plane side wall 114 and be positioned such that at least a portion of guide surface 120a can contact a surgical instrument passing through slot 100. As the surgical instrument is inserted into slot 100 and engages guide surface 120a, a force may be applied by the instrument to guide surface 120a, and flexing portion 122a may flex in response to the applied force, thereby allowing at least a portion of guide surface 120a to move substantially away from cutting-plane side wall 114 and permit the surgical instrument to travel therebetween. In some embodiments, the spring-fit structure may flex so as to form-fit the surgical instrument. Guide surface 120a can apply to the surgical instrument a force directed, for example, substantially towards the cutting-plane side wall 114. The force applied to the surgical instrument may, for example, provide improved consistency and/or stability of contact between the surgical instrument and one or more portions of the cutting-plane side wall 114, such as, for example, portions within the predetermined cutting plane 112 (e.g., 118a, 118b) and/or may provide resistance to the surgical instrument deviating from predetermined cutting plane 112.

Figure 3:
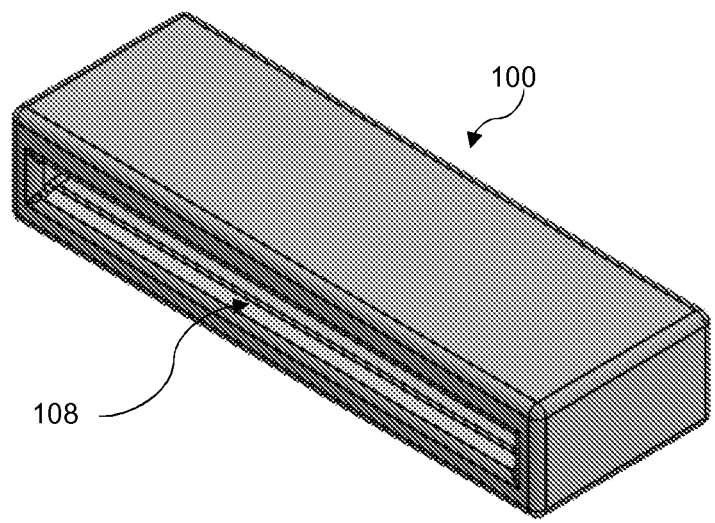
FIG. 3 is a perspective view of a second exemplary guide slot embodiment.
Figure 4:
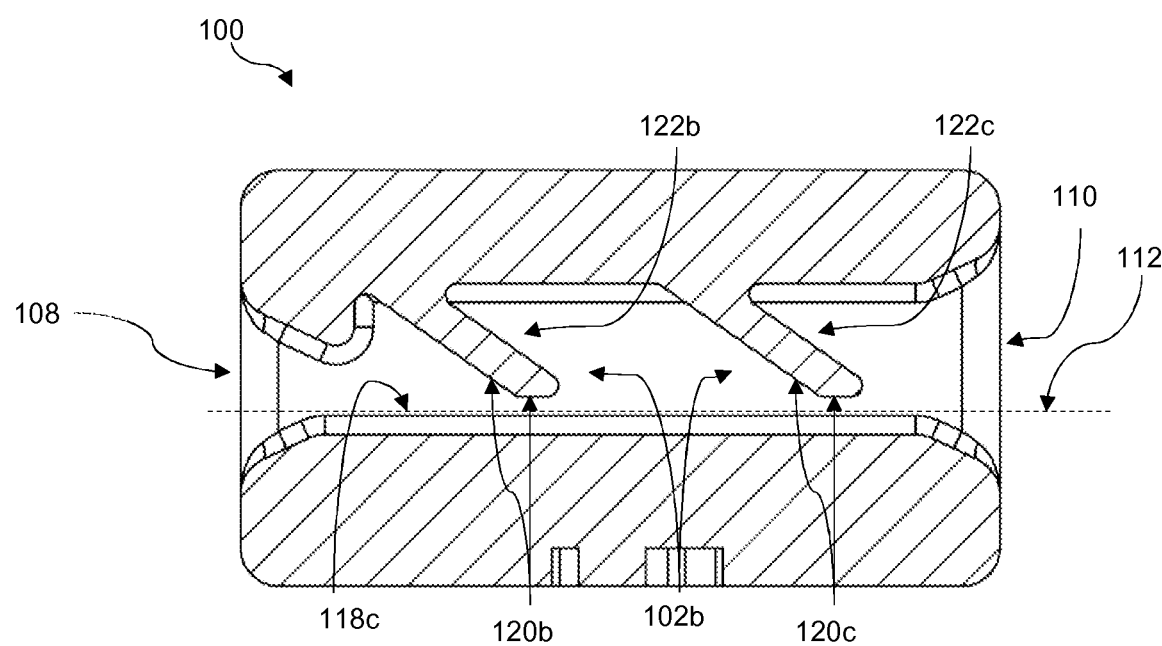
FIG. 4 is a cross-sectional view of the guide slot embodiment of FIG. 3 in a plane substantially perpendicular to entrance opening 108.

As will be appreciated, in various embodiments, the flexing or spring portion of the spring-fit structures can incorporate a variety of spring-type structures or shapes, such as, for example, that of a coil spring, helical spring, cantilever spring, leaf spring, flat spring, and/or machined spring. For example, in some embodiments, the spring-fit structure can comprise a cantilevered leaf spring configuration, as shown in FIGS. 1 and 2. Accordingly, in some embodiments, guide surface 120a may comprise a surface of the flexing portion 122a, or a portion thereof. Optionally, a recess may be formed in the opposing side wall 116 to accommodate one or more portions of the spring-fit structure 120a and/or movement of one or more portions of the spring-fit structure 120a when engaged by a surgical instrument. Also optionally, some embodiments can include one or more additional openings 126, which can, for example, provide a channel(s) that facilitates removal of manufacturing material (e.g., unfused powder in the case of an SLS manufacturing process) and/or facilitate heat dissipation during use. In some embodiments, guide surface 120a, or at least a portion thereof, can be substantially convex in at least one plane. A convex guide surface may reduce contact area between the surgical instrument and spring-fit structure 102a, and may thereby reduce friction and heat generation associated with engagement of the surgical instrument with spring-fit structure 102a. Alternatively or in addition, in some embodiments, guide surface 120 may include one or more substantially straight portions (e.g., 120b of FIG. 4) and/or include one or more concave portions. Furthermore, some embodiments may include multiple flexing portions 122 and/or multiple guide surfaces 120. For example, FIGS. 3 and 4 depict an embodiment of slot 100 that includes first flexing portion 122b and first guide surfaces 120b and also includes second flexing portion 122c and second guide surfaces 120c.

Figure 5:
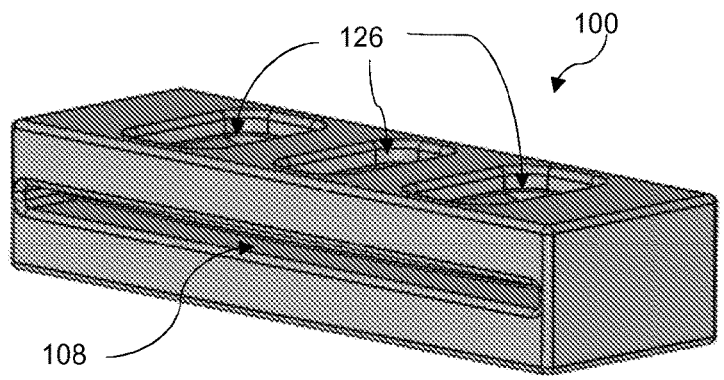
FIG. 5 is a perspective view of a third exemplary guide slot embodiment.
Figure 6A:
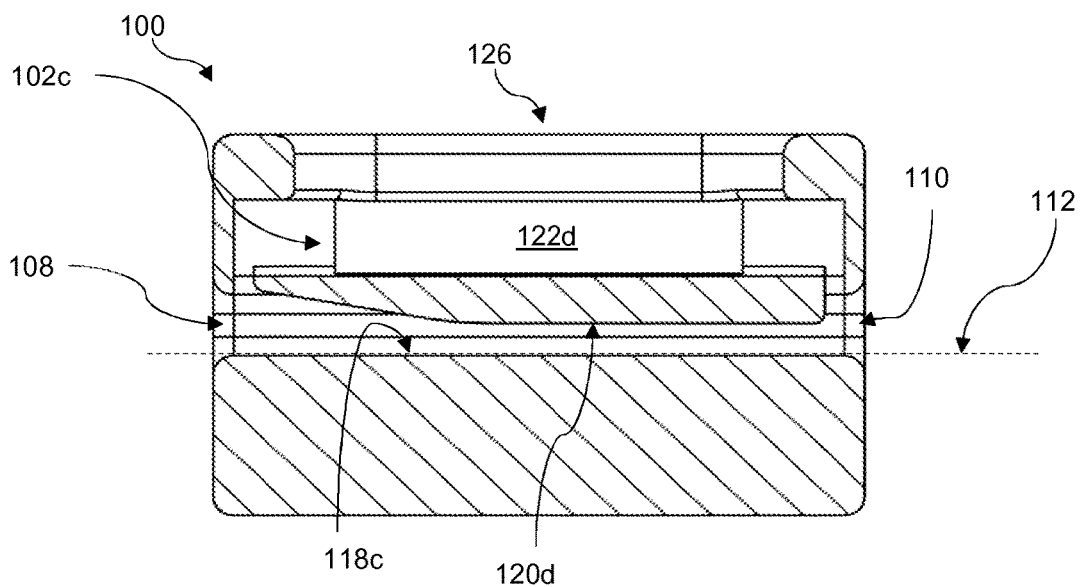
FIG. 6a is a cross-sectional view of the guide slot embodiment of FIG. 5 in a plane substantially perpendicular to entrance opening 108.
Figure 6B:
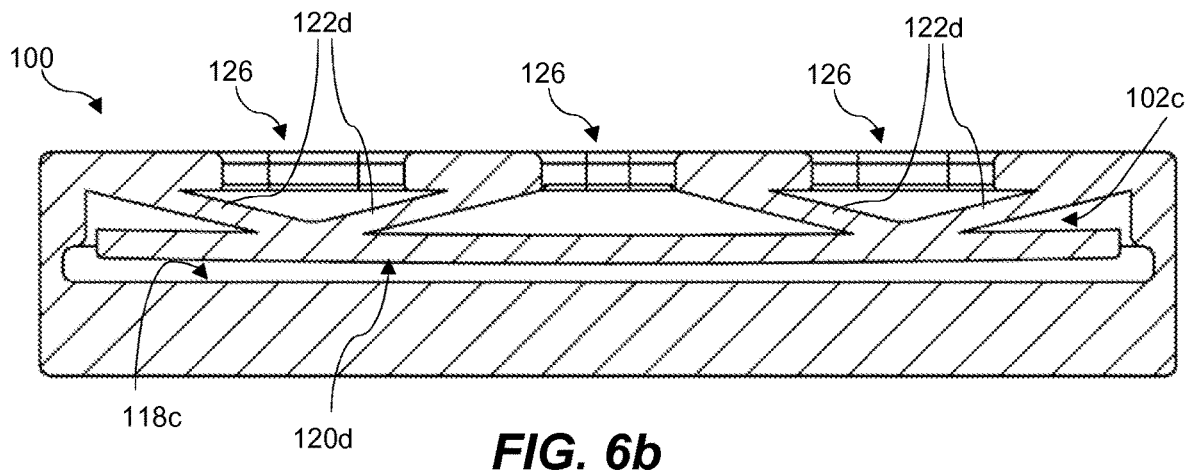
FIG. 6b is a cross-sectional view of the guide slot embodiment of FIG. 5 in a plane substantially parallel to entrance opening 108.

Additionally or alternatively, in some embodiments, a guide surface 120d (or at least a portion thereof) can be a substantially flat surface oriented substantially parallel to predetermined cutting plane 112 and supported by one or more flexing portions 122d, which connect guide surface 120d to the body of the guide, as shown, for example, in FIGS. 5, 6a, and 6b. For example, flexing portions 122d can comprise struts positioned oblique to guide surface 120d in at least one plane (e.g., a plane substantially transverse to predetermined cutting plane 112, as can be seen in FIG. 6b, which depicts a cross-section of the slot of FIGS. 5 and 6a in a plane transverse to cutting plane 112 and an axis connecting entrance opening 108 and exit opening 110). Flexing potion(s) 122d can comprise alternative spring structures, such as, for example, a coil spring, a helical spring, etc. In some embodiments, flexing portion(s) 122d may be integrally formed with guide surface 120d, while in other embodiments the components may be modular.

Figure 7A:
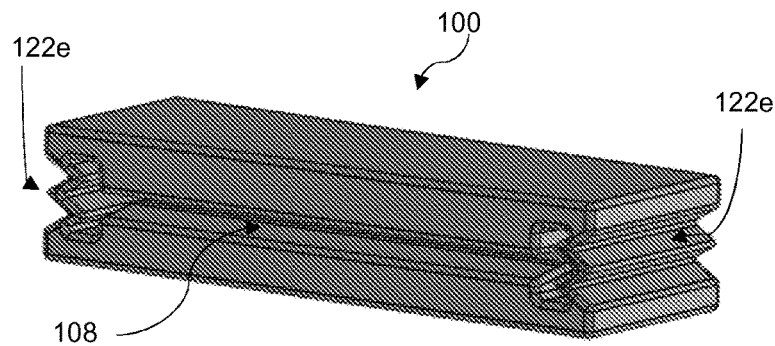
FIG. 7a is a perspective view of a fourth exemplary guide slot embodiment.
Figure 7B:
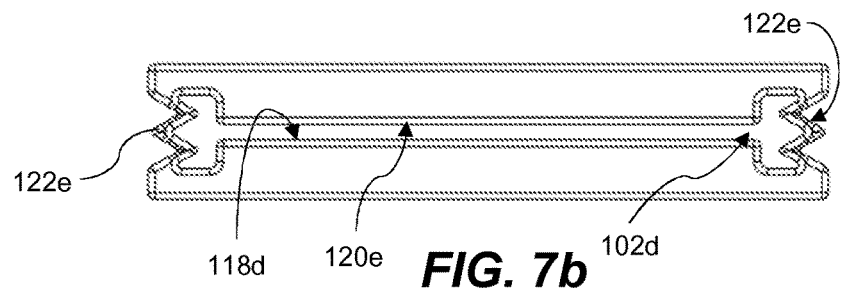
Figure 8A:
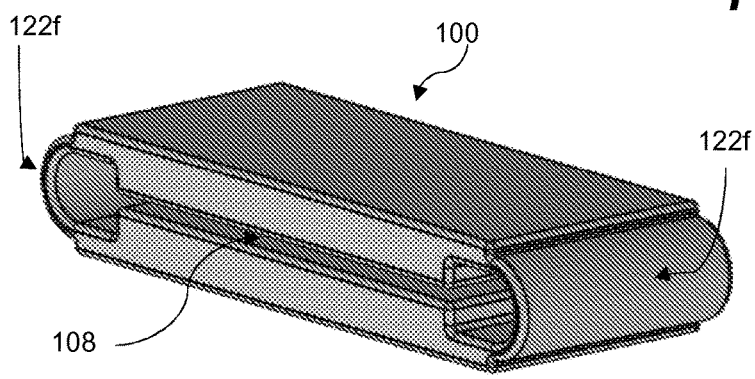
FIG. 8a is a perspective view of a fifth exemplary guide slot embodiment.
Figure 8B:
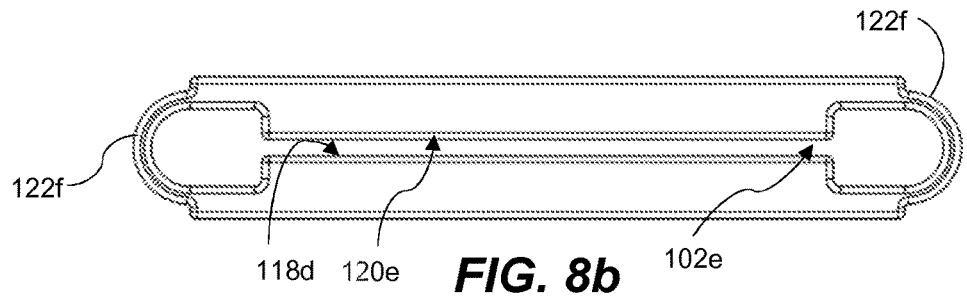
Figure 9:
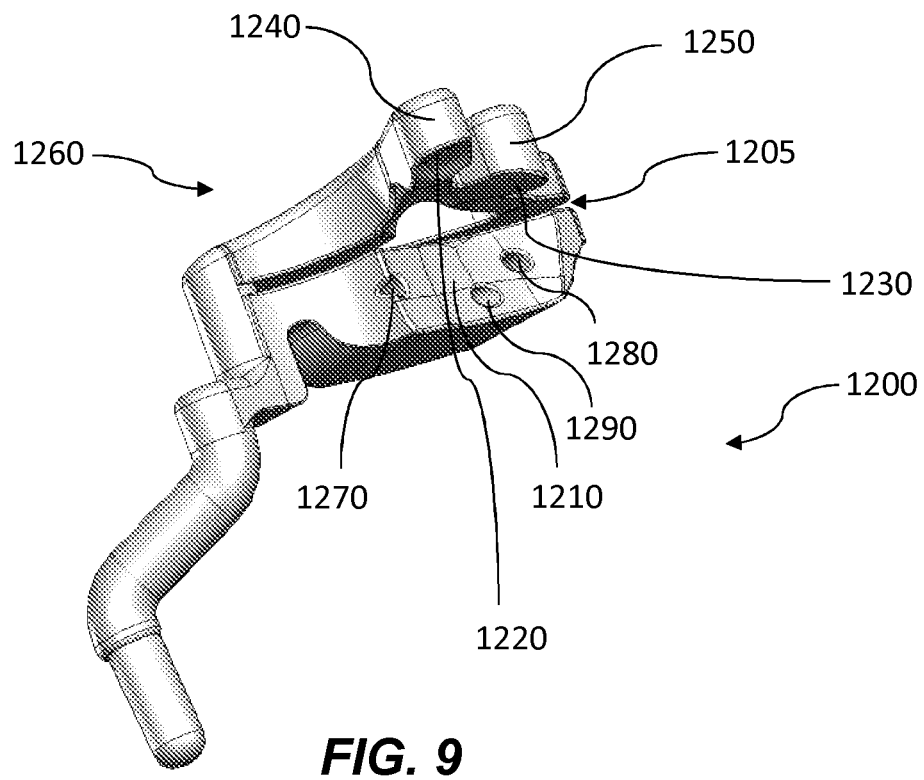
FIG. 9 is a perspective view of an exemplary embodiment of a tibial jig.

Additionally or alternatively, in some embodiments one or more flexing portions can comprise at least a portion of a sidewall of slot 100. For example, in some embodiments, one or more sidewalls of slot 100 can comprise a tension spring structure, such as, for example, an accordion-type spring structure 122e (depicted in FIGS. 7a and b) or a flexible curved or loop structure 122f (as depicted in FIGS. 8a and b). In some such embodiments, slot 100 may be dimensioned such that a distance between guide surface 120e and at least a portion of a surface 118d of cutting-plane side wall 114 is less than a width and/or a kerf of a surgical instrument to be inserted through slot 100. Accordingly, in some embodiments, the one or more flexing portions incorporated into sidewall(s) of slot 100 can allow for slot 100 to expand (e.g., between guide surface 120e and side wall 114) upon insertion of the surgical instrument to form fit the slot to the surgical instrument.

In various embodiments, one or more dimensions, properties, and/or parameters associated with one or more spring-fit structures can be varied to achieve a desired guidance provided by the slot to a surgical instrument and/or based on material properties of portions of the spring-fit structure. For example, the working length of a flexing or spring portion may be selected or designed such that the guide surface will be able to move to a desired maximum distance without the flexing or spring portion yielding. Similarly, the thickness of a flexing or spring portion may be selected to be thick enough to provide a desired minimum strength and/or resistance to movement, but thin enough to flex without material yielding. In some embodiments, the flexing or spring portion may have a uniform thickness throughout the working length. Alternatively, the flexing or spring member may have a non-uniform thickness, such as, for example, a tapered thickness, which may provide more uniform stress concentrations during bending. Additionally or alternatively, in some embodiments, one or more portions of the spring-fit structure may be filleted, such as, for example, at junctures where the flexing portion connects to the body of the guide. Such fillets may reduce stress at particular locations. Additionally or alternatively, the elasticity and/or resistance associated with a flexing or spring portion may be selected, designed, and/or modified using materials and processes known in the art. For example, various types and/or combinations of polymers and polymer manufacturing techniques, as discussed further below, can be used to make a spring-fit structure with a desired elasticity and/or resistance.

Furthermore, the location of one or more spring-fit structures relative to the slot 100 can be varied to achieve desired guidance characteristics provided by the slot to a surgical instrument and/or based on material properties of portions of the spring-fit structure. For example, a spring-fit structure, such as spring-fit structure 102a, may be positioned relatively close or adjacent to entrance opening 108 of slot 100. This positioning may provide for easier insertion of the surgical instrument into slot 100 and/or may provide more resistance (e.g., relative to a spring-fit structure positioned closer to exit opening 110) to deviation of portions of the surgical instrument through and/or below the predetermined cut plane 112 after exiting slot 100. In cases where the surgical instrument comprises a saw, deviation of portions of the saw blade through and/or below predetermined cut plane 112 may result in overcutting (e.g., resecting more tissue than intended, cutting tissue at a greater depth than intended). Additionally or alternatively, positioning a spring-fit structure 102 relatively close or adjacent to exit opening 110 of slot 100 may provide increased resistance to deviation of portions of the surgical instrument upwards and/or away from predetermined cut plane 112. In some embodiments a slot 100 may include a first spring-fit structure proximate to entrance opening 108 and a second spring-fit structure proximate to exit opening 110. Additionally or alternatively, some embodiments of slot 100 can include a spring-fit structure positioned substantially equidistant from entrance opening 108 and exit opening 110.

Various embodiments may further include in the side walls of slot 100 one or more substantially concave portions, scallops, indentations, or other surface features that provide additional space or clearance along a particular portion of a side wall. For example, as depicted in FIGS. 1 and 2, some embodiments can include a substantially concave portion (hereafter referred to as a "scallop") 124 in cutting-plane side wall 114. Scallop 124 may be positioned substantially adjacent to or opposite spring-fit structure 102a. In such embodiments, scallop 124 may reduce or eliminate undesired scraping (e.g., by a cutting edge of a saw) of a portion of spring-fit structure 102a (e.g., guide surface 120a) as the surgical instrument passes through slot 100. Optionally, in some embodiments, scallop 124 may be designed based on a width and/or a kerf (e.g., of a saw blade) of a surgical instrument. Additionally or alternatively, some embodiments may include a scallop that is positioned substantially offset from spring-fit structure 102. In various embodiments, the incorporation of one or more scallops may reduce contact area between the surgical instrument and slot 100, and may thereby reduce friction and heat generation associated with passing the surgical instrument through slot 100.

Jigs and/or guide slots described herein may include slots that are dimensioned to accommodate various cutting tools and/or manufacturing materials and/or tolerances. For example, a guide slot may be designed for a saw blade with a body thickness of 1.10 mm and a saw blade kerf of 1.3 mm. A guide slot may be made using an SLS process with a manufacturing tolerance of ±0.3 mm. An exemplary guide slot embodiment intended to accommodate these parameters and utilizing a spring-fit structure comprising a curved, cantilevered leaf spring (as illustrated in FIGS. 1 and 2) can include entrance and exit opening depths (i.e., dimension orthogonal to the cutting plane) of 1.6 mm, a minimum depth between the guide surface of the leaf spring (in uncompressed state) and the cutting plane of 1.0 mm, and a maximum depth between the cutting plane and the surface of the scallop of 0.6 mm.

Various embodiments disclosed herein include systems, methods, and devices for performing a series of bone cuts to receive a patient-adapted implant. Specifically, a set of jigs can be designed in connection with the design of a patient-adapted implant component. The designed jigs can guide the surgeon in performing one or more patient-adapted cuts to the bone so that those cut bone surface(s) negatively-match patient-adapted bone-facing surfaces of corresponding patient-adapted implant components.

Spring-fit guide slots (i.e., guide slots with spring-fit structures, such as, for example, any of the embodiments described above) can be incorporated into a variety of surgical guide tools, including, for example, those disclosed in U.S. patent application Ser. No. 13/397,457, entitled "Patient-Adapted and Improved Orthopedic Implants, Designs And Related Tools," filed Feb. 15, 2012, and published as U.S. Patent Publication No. 2012-0209394 and/or those disclosed in International Application No. PCT/US2013/025216, entitled "Joint Arthroplasty Devices, Systems, and Methods," filed Feb. 7, 2013, and published as International Publication No. WO2013/119865, which is incorporated herein by reference in its entirety. For example, spring-fit guide slots can be incorporated into, or in place of, captured cutting guide slots, uncaptured cutting guide surfaces, and/or guide holes/apertures (e.g., for guiding drills, pins, etc.). Further, spring-fit guide slots can be incorporated into patient-specific guide tools, as well as standard (i.e., not patient-specific) guide tools. Several exemplary embodiments of surgical repair systems and surgical guide tools incorporating one or more spring-fit guide slots are described in further detail below.

Various embodiments of surgical repair systems can include implants and procedures where the implant has an inner, bone-facing surface and an outer, joint-facing surface, and the inner, bone-facing surface engages an articular surface (and/or surgically-prepared tissue surface(s) proximate to locations where at least a portion of tissue comprising an articular surface has been resected) of a first biological structure (e.g., bone or cartilage) at a first interface. The articular surface can be a native surface, a cut surface, a preexisting implant component and/or various combinations and/or quantities/distributions thereof (e.g., multiple cut planes separated by a region of natural subchondral bone and/or articular cartilage). In addition, an outer, joint-facing surface of one implant component can oppose a second, outer joint-facing surface on an opposing joint implant component at a joint interface. In certain embodiments, one or more features of the implant component, for example, various inner, bone-facing surfaces and/or various outer, joint-facing surfaces can be patient-adapted (i.e., comprising one or more patient-specific and/or patient-engineered features).

Some embodiments of surgical repair systems can include the use of a guide tool having at least one patient-specific bone-facing surface portion that substantially negatively-matches at least a portion of a biological surface at the patient's joint. The guide tool further can include at least one aperture or slot for directing movement of a surgical instrument (e.g., securing pin, cutting tool). One or more of the slots can be designed to guide the surgical instrument to deliver a patient-optimized placement for, for example, a securing pin or resection cut. In addition or alternatively, one or more of the slots can be designed to guide the surgical instrument to deliver a standard placement for, for example, a securing pin or resection cut. As used herein, "jig" also can refer to guide tools, for example, to guide tools that guide resectioning of a patient's biological structure.

FIGS. 9 and 10a-c depict views of an exemplary embodiment of a tibial jig 1200 that can be used for preparing a proximal tibia to receive one or more implant components. In some embodiments, tibial jig 1200 can include one or more surfaces designed and/or selected to accommodate and/or conform to various anatomical features and/or surfaces of the underlying tibial anatomy. For example, tibial jig 1200 can include a substantially posterior-oriented or facing surface 1210 and one or more caudad-oriented or capping surfaces 1220 and 1230 formed on projections 1240 and 1250 that extend from an upper portion 1260 of the tibial jig 1200. Surface 1210 can be designed based on patient-specific information to have a shape to substantially conform to and/or negatively match an anterior-facing portion of the tibial head when positioned against it, with the capping surfaces 1220 and 1230 conforming to and/or negatively matching corresponding subchondral bone surfaces of the proximal tibia (not shown). When properly positioned on the tibia in conforming alignment, this arrangement and placement can result in alignment of the tibial jig 1200 in a known position and/or orientation.

Figure 10A:
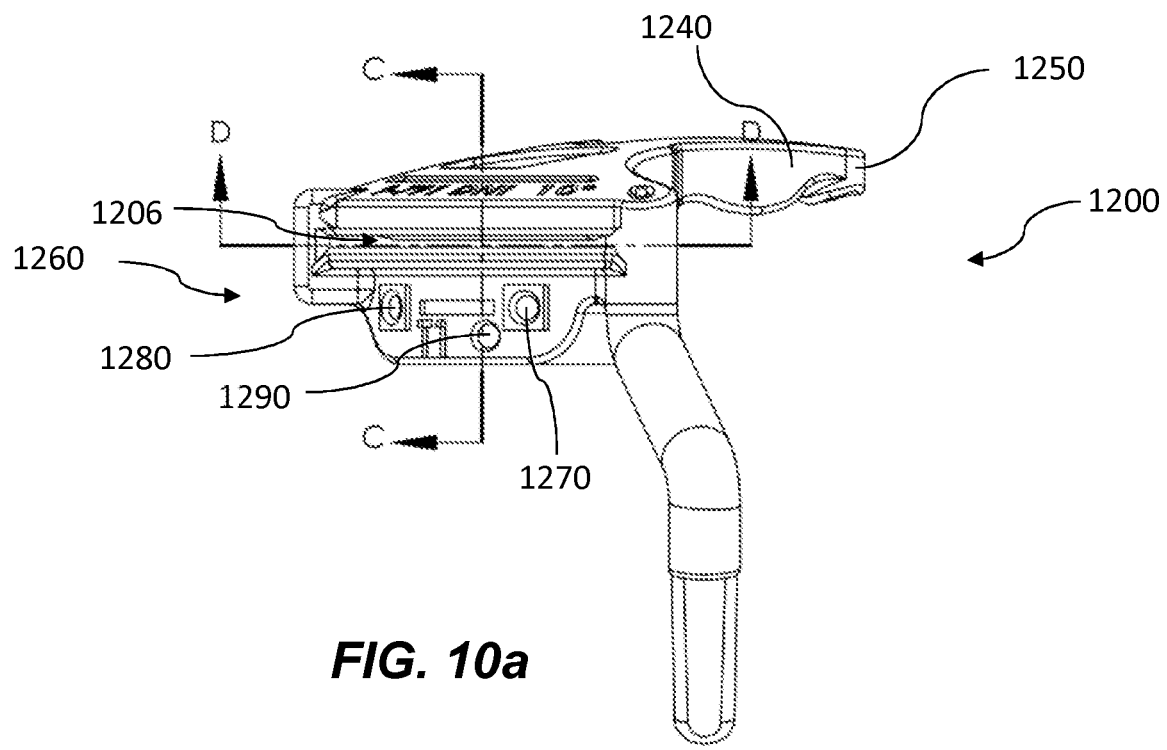
FIG. 10a is a side view of the tibial jig embodiment of FIG. 9.
Figure 10B:
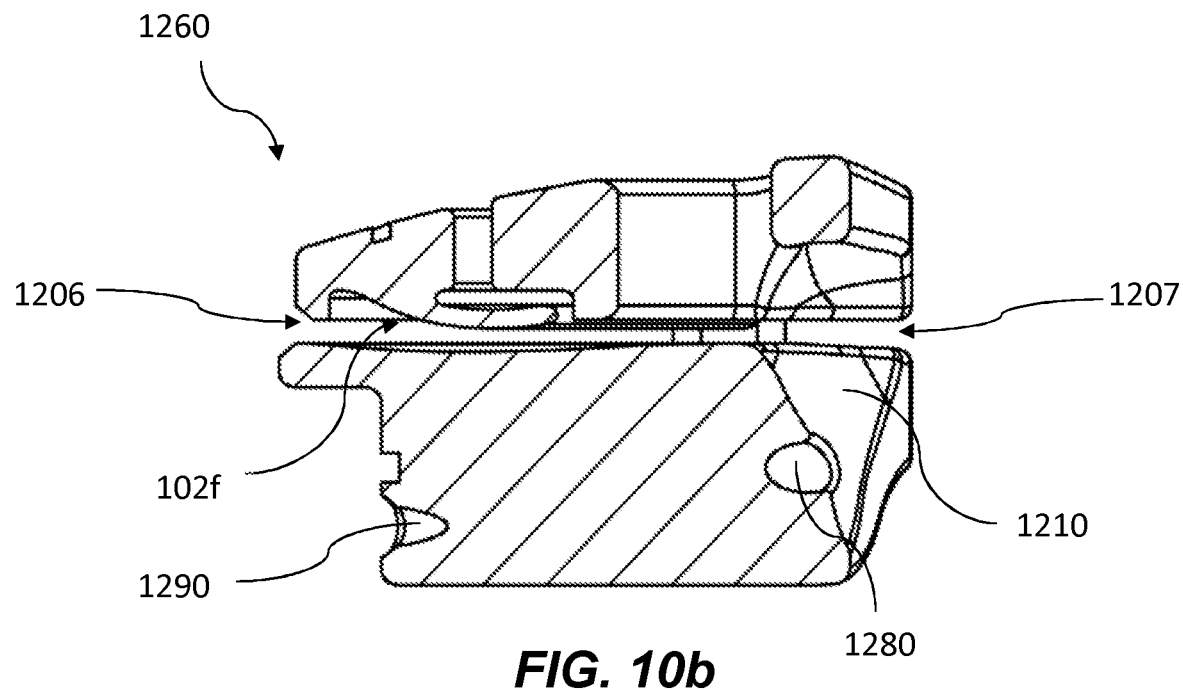
FIG. 10b is a cross-sectional view of upper portion 1260 of the tibial jig embodiment of FIGS. 9 and 10a as indicated by C.
Figure 10C:
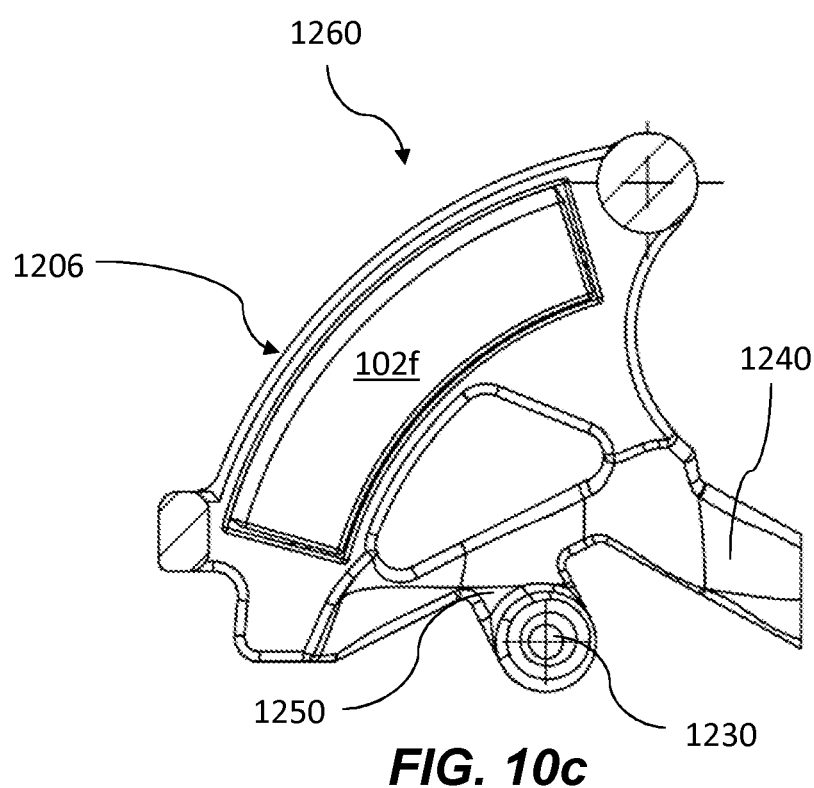
FIG. 10c is a cross-sectional view of upper portion 1260 of the tibial jig embodiment of FIGS. 9 and 10a as indicated by D.

In some embodiments, tibial jig 1200 can further include one or more slots 1205, 1270, 1280 and 1290, which can be configured to guide insertion of surgical instruments (e.g., one or more cutting or drilling instrument, alignment pins, wires) into the tibia to cut, align, and/or secure the jig (or various other tools) to the tibia. For example, in some embodiments, tibial jig 1200 can include a slot 1205 that is configured to guide a surgical cutting tool in resection of the proximal tibia along a cutting plane having a predetermined position and orientation when jig 1200 is positioned in conforming alignment with the proximal tibia. The predetermined cutting plane may have a position and orientation such that the resulting cut tibia is configured to receive a tibial implant component (e.g., a patient adapted implant component, a standard implant component). Slot 1205 can be designed to incorporate a spring-fit structure, such as, for example, any one or more of the embodiments described above, to enhance guidance of the surgical instrument. For example, slot 1205 can include a spring fit structure 102*f*, which comprises a cantilevered leaf spring configuration (e.g., similar to that shown in FIGS. 1 and 2), as illustrated in FIG. 10*b*. In some embodiments, a leaf spring component of spring-fit structure 102*f* can be substantially curved (e.g., as depicted in FIG. 10*c*) in a plane substantially parallel to the cutting plane of slot 1205 to substantially follow the curvature of a portion of the body of jig 1200 and/or of an entrance opening 1206 of slot 1205. Additionally, in some embodiments, an exit opening 1207 of slot 1205 may be located within patient-specific surface 1210.

Figure 11A:
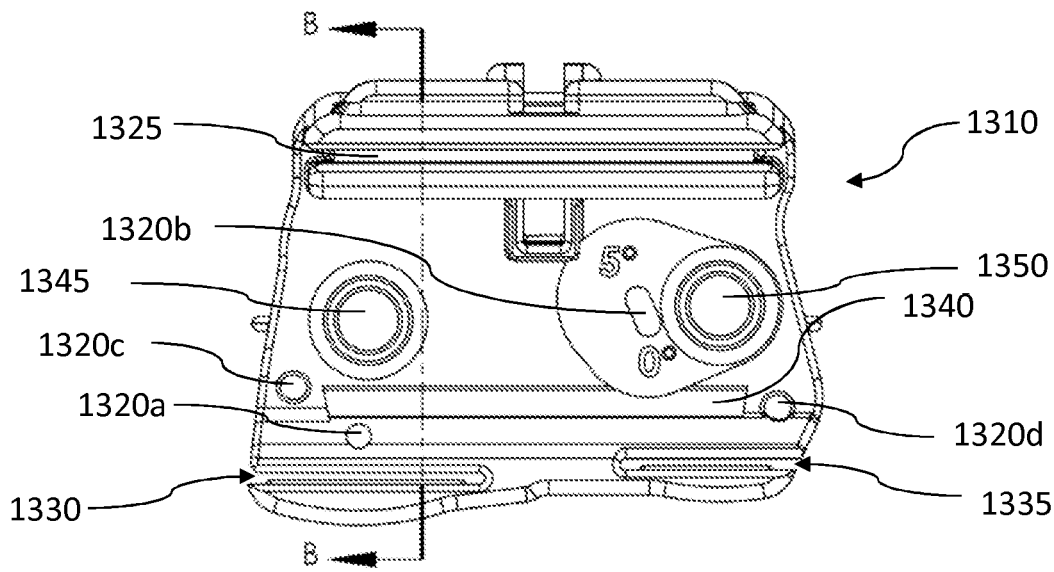
FIG. 11a is a front view of an exemplary embodiment of a femoral jig.

FIGS. 11*a* and *b* depict views of an exemplary embodiment of a femoral jig 1310 that can be used for preparing a distal femur to receive one or more implant components. Femoral jig 1310 can include one or more surfaces 1315 configured for placement on one or more distal cut planes formed on the distal femur. One or more portions of the perimeter of femoral jig 1310 can optionally be shaped to substantially align with respective portions of the perimeter of the resected distal femur. Femoral jig 1310 can further include one or more guide slots, such as, for example, drill and/or pin holes 1320*a-d*, which can be configured to guide and/or receive one or more pins inserted into and/or extending from the cut femur and which may be used for alignment and/or securement of femoral jig 1310 with respect to the femur. Optionally, femoral jig 1310 can include drill guides 1345 and 1350 that can be employed to form a medial bore and a lateral bore in the resected distal surface of the femur to accommodate pegs or anchors of the femoral implant component(s).

Figure 11B:
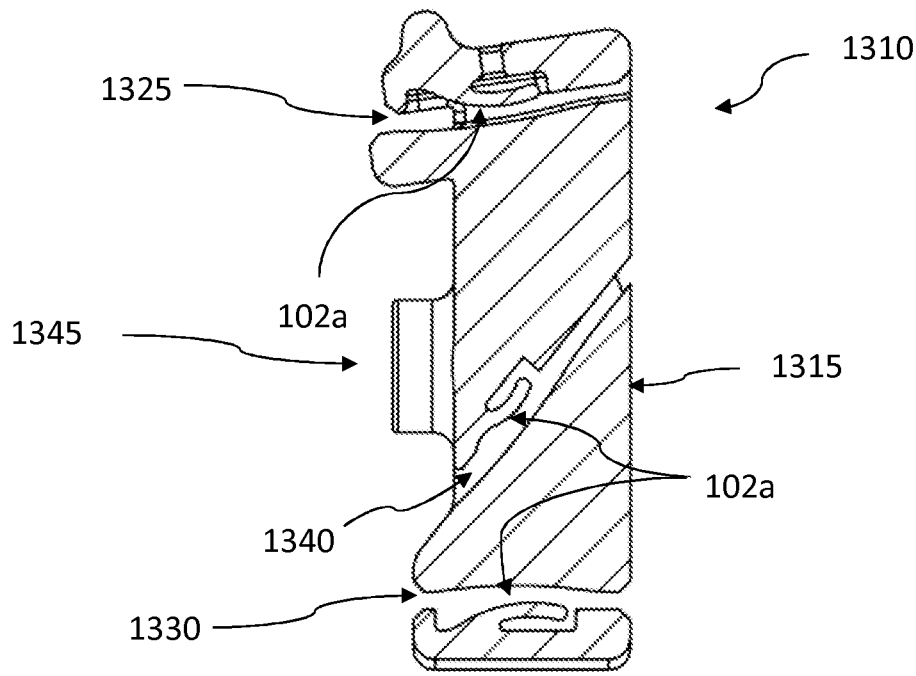
FIG. 11b is a cross-sectional view of the femoral jig embodiment of FIG. 11a as indicated by B.

Additionally or alternatively, femoral jig 1310 can include one or more guide slots for guiding surgical cutting tools in resection of various portions of the femur. For example, femoral jig 1310 can include an anterior guide slot 1325 that is configured to guide a saw in creating an anterior bone cut on the distal femur. Femoral jig 1310 may also include a medial posterior guide slot 1330 and a lateral posterior guide slot 1335, configured to guide a saw in creating a posterior bone cut on the medial and lateral condyles, respectively, of the distal femur. Femoral jig 1310 may further include an anterior chamfer guide slot 1340, configured to guide a cutting saw in creating an anterior chamfer bone cut on the distal femur. Each of the resulting bone cuts may correspond to, negatively match, and/or be configured to receive a respective bone-facing surface of a femoral implant component. Each of the guide slots may be a partially captured slot (e.g., medial and lateral posterior guide slots 1330 and 1340, as depicted in FIG. 11*a*) or a fully captured slot (e.g., anterior guide slot 1325 and anterior chamfer guide slot 1340 as depicted in FIG. 11*a*). Furthermore, one or more of the guide slots 1325, 1330, 1335, and 1340 can be designed to incorporate a spring-fit structure, such as, for example, those discussed above. For example, in some embodiments, each of slots 1325, 1330, 1335, and 1340 can include a spring-fit structure 102*a*, which comprises a cantilevered leaf spring configuration (e.g., similar to that shown in FIGS. 1 and 2), as illustrated in FIG. 11*b*.

In various embodiments, the slots in a particular guide tool can be substantially horizontal, substantially diagonal, or substantially vertical, for example, as compared to the patient's mechanical axis and/or anatomical axis. Moreover, one or more of the resection cut slots can allow for a complete resection cut or a partial resection cut, e.g., scoring of the patient's bone to establish a resection cut that can be finished after removing the tool. This approach can be advantageous by allowing for faster resection in the absence of the guide tool. Moreover, one or more resection cut slots can include a blade-depth or drill-depth stop. This is particularly useful for step resection cuts, for example, vertical step resection cuts, that connect two facets or planes of a resected surface.

While some exemplary embodiments provided above are generally described with respect to treatment of a knee joint, various aspects and embodiments disclosed herein can equally be applied to treatment of any anatomical feature and/or joint. For example, various embodiments of the guide tools, guide slots, and/or spring-fit structures disclosed herein can be configured for use in treatment of any particular joint, including, without limitation, a spine, spinal articulations, an intervertebral disk, a facet joint, a shoulder, an elbow, a wrist, a hand, a finger, a hip, a knee, an ankle, a foot, or a toe joint. This can include patient-adapted and/or standard guide tools that incorporate one or more spring-fit guide slots. Likewise, methods of designing (e.g., designing and making) and/or using the guide tools, guide slots, and/or spring-fit structures, as described herein, as well as associated implant components, can be applied to treatment of any anatomical feature or joint.

The step of designing an implant component and/or guide tool (including one or more slots with spring-fit structures) as described herein can include both configuring one or more features, measurements, and/or dimensions of the implant and/or guide tool (e.g., derived from patient-specific data from a particular patient and adapted for the particular patient) and manufacturing the implant and/or guide tool. In certain embodiments, manufacturing can include making the implant component and/or guide tool from starting materials, such as, for example, metals and/or polymers or other materials in solid (e.g., powders or blocks) or liquid form. In addition or alternatively, in certain embodiments, manufacturing can include altering (e.g., machining) an existing implant component and/or guide tool, for example, a standard blank implant component and/or guide tool or an existing implant component and/or guide tool (e.g., selected from a library).

The manufacturing techniques used for making or altering an implant component and/or guide tool can include any techniques known in the art today and in the future. Such techniques include, but are not limited to, additive as well as subtractive methods, i.e., methods that add material, for example to a standard blank, and methods that remove material, for example from a standard blank. Various technologies and techniques appropriate for manufacturing implants and guide tools can include, for example, those summarized in Table 1.

TABLE 1

Exemplary technologies for manufacturing implants and/or guide tools.

| Technique | Brief description of technique and related notes |
|---|---|
| CNC | CNC refers to computer numerically controlled (CNC) machine tools, a computer-driven technique, e.g., computer-code instructions, in which machine tools are driven by one or more computers. Embodiments of this method can interface with CAD software to streamline the automated design and manufacturing process. |
| CAM | CAM refers to computer-aided manufacturing (CAM) and can be used to describe the use of software programming tools to efficiently manage manufacturing and production of products and prototypes. CAM can be used with CAD to generate CNC code for manufacturing three-dimensional objects. |
| Casting, including casting using rapid prototyped casting patterns | Casting is a manufacturing technique that employs a mold. Typically, a mold includes the negative of the desired shape of a product. A liquid material is poured into the mold and allowed to cure, for example, with time, cooling, and/or with the addition of a solidifying agent. The resulting solid material or casting can be worked subsequently, for example, by sanding or bonding to another casting to generate a final product. |
| Welding | Welding is a manufacturing technique in which two components are fused together at one or more locations. In certain embodiments, the component joining surfaces include metal or thermoplastic and heat is administered as part of the fusion technique. |
| Forging | Forging is a manufacturing technique in which a product or component, typically a metal, is shaped, typically by heating and applying force. |
| Rapid prototyping | Rapid prototyping refers generally to automated construction of a prototype or product, typically using an additive manufacturing technology, such as EBM, SLS, SLM, SLA, DMLS, 3DP, FDM and other technologies |
| EBM ® | EBM ® refers to electron beam melting (EBM ®), which is a powder-based additive manufacturing technology. Typically, successive layers of metal powder are deposited and melted with an electron beam in a vacuum. |
| SLS | SLS refers to selective laser sintering (SLS), which is a powder-based additive manufacturing technology. Typically, successive layers of a powder (e.g., polymer, metal, sand, or other material) are deposited and melted with a scanning laser, for example, a carbon dioxide laser. |
| SLM | SLM refers to selective laser melting ™ (SLM), which is a technology similar to SLS; however, with SLM the powder material is fully melted to form a fully-dense product. |
| SLA or SL | SLA or SL refers to stereolithography (SLA or SL), which is a liquid-based additive manufacturing technology. Typically, successive layers of a liquid resin are exposed to a curing, for example, with UV laser light, to solidify each layer and bond it to the layer below. This technology typically requires the additional and removal of support structures when creating particular geometries. |
| DMLS | DMLS refers to direct metal laser sintering (DMLS), which is a powder-based additive manufacturing technology. Typically, metal powder is deposited and melted locally using a fiber optic laser. Complex and highly accurate geometries can be produced with this technology. This technology supports net-shaping, which means that the product generated from the technology requires little or no subsequent surface finishing. |
| LC | LC refers to LaserCusing ®(LC), which is a powder-based additive manufacturing technology. LC is similar to DMLS; however, with LC a high-energy laser is used to completely melt the powder, thereby creating a fully-dense product. |
| 3DP | 3DP refers to three-dimensional printing (3DP), which is a high-speed additive manufacturing technology that can deposit various types of materials in powder, liquid, or granular form in a printer-like fashion. Deposited layers can be cured layer by layer or, alternatively, for granular deposition, an intervening adhesive step can be used to secure layered granules together in bed of granules and the multiple layers subsequently can be cured together, for example, with laser or light curing. |
| LENS | LENS ® refers to Laser Engineered Net Shaping ™ (LENS ®), which is a powder-based additive manufacturing technology. Typically, a metal powder is supplied to the focus of the laser |

TABLE 1-continued

Exemplary technologies for manufacturing implants and/or guide tools.

| Technique | Brief description of technique and related notes |
| --- | --- |
| | beam at a deposition head. The laser beam melts the powder as it is applied, in raster fashion. The process continues layer by and layer and requires no subsequent curing. This technology supports net-shaping, which means that the product generated from the technology requires little or no subsequent surface finishing. |
| FDM | FDM refers to fused deposition modeling ™ (FDM) is an extrusion-based additive manufacturing technology. Typically, beads of heated extruded polymers are deposited row by row and layer by layer. The beads harden as the extruded polymer cools. |

Currently, implant components and/or guide tools of joint repair systems often employ metal and/or polymeric materials. A wide-variety of metals can be used in the practice of the embodiments described herein, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol T™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

A wide-variety of polymers can additionally or alternatively be used in the practice of the embodiments described herein. Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. Other appropriate materials include, for example, the polyketone known as polyetheretherketone (PEEK).

In various embodiments, the body and/or guide surfaces of guide slots, spring-fit structures, and/or surgical guides may comprise metals, plastics, ceramics or various combinations thereof.

The various descriptions contained herein are merely exemplary in nature and, thus, variations that do not depart from the gist of the teachings are intended to be within the scope of the teachings. Such variations are not to be regarded as a departure from the spirit and scope of the teachings, and the mixing and matching of various features, elements and/or functions between various embodiments is expressly contemplated herein. One of ordinary skill in the art would appreciate from this disclosure that features, elements and/or functions of one embodiment may be incorporated into another embodiment as appropriate, unless described otherwise above. Many additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A system for treatment of a joint of a patient, the system comprising:
    a first guide for a surgical instrument; and
    an implant component to be implanted in the joint,
    wherein the first guide comprises:
        a body having a guide slot extending through at least a portion of the body from a first side of the body to a second side of the body,
    wherein the guide slot is configured to receive the surgical instrument through an entrance opening and guide the surgical instrument along a path extending from an exit opening in a direction substantially opposite the entrance opening and substantially along a predetermined cutting plane,
    wherein the entrance opening is located on the first side of the body and the exit opening is located on the second side of the body,
    wherein a cutting-plane side wall of the guide slot includes at least a portion substantially located within the cutting plane,
    wherein an opposing side wall of the guide slot is positioned substantially opposite the cutting-plane side wall and includes at least one spring-fit structure, the at least one spring-fit structure comprising:
        a guide surface substantially facing the cutting-plane side wall; and
        a flexing portion connected to the body and supporting at least a portion of the guide surface, the flexing portion configured to allow at least a portion of the guide surface to move in a direction away from the cutting plane when the surgical instrument is inserted into the guide slot and contacts at least a portion of the guide surface, and
    wherein the body further comprises at least one alignment surface having at least a portion with a shape based, at least in part, on patient-specific information regarding a surface of the patient's joint such that the guide can be positioned against and aligned with the corresponding surface of the patient's joint in a predetermined position and/or orientation, the alignment surface making up at least a portion of the second side of the body.

2. The system of claim 1, wherein the implant includes at least one bone-facing surface and wherein the guide slot is configured to guide a saw along the predetermined cutting plane such that a resected surface of the joint is formed and configured to support the at least one bone-facing surface of the implant.

3. The system of claim 1, wherein the implant includes at least one bone-facing surface and wherein the guide slot is configured to guide a saw along the predetermined cutting plane such that a resected surface of the joint is formed that substantially negatively matches the at least one bone-facing surface of the implant.

4. A guide for a surgical instrument for use in treating a joint of a patient, the guide comprising:
   a body having a guide slot extending through at least a portion of the body from a first side of the body to a second side of the body,
   wherein the guide slot is dimensioned to receive the surgical instrument through an entrance opening and guide the surgical instrument along a path extending from an exit opening in a direction substantially opposite the entrance opening and substantially along a predetermined cutting plane,
   wherein the entrance opening is located on the first side of the body and the exit opening is located on the second side of the body,
   wherein a cutting-plane side wall of the guide slot includes at least a portion substantially located within the cutting plane,
   wherein an opposing side wall of the guide slot is positioned substantially opposite the cutting-plane side wall and includes at least one spring-fit structure, the at least one spring-fit structure comprising:
      a guide surface substantially facing the cutting-plane side wall; and
      a flexing portion connected to the body and supporting at least a portion of the guide surface, the flexing portion configured to allow at least a portion of the guide surface to move in a direction substantially away from the cutting plane when the surgical instrument is inserted into the guide slot and contacts at least a portion of the guide surface, and
   wherein the body further comprises at least one alignment surface having at least a portion with a shape based, at least in part, on patient-specific information regarding a surface of the patient's joint such that the guide can be positioned against and aligned with the corresponding surface of the patient's joint in a predetermined position and/or orientation, the alignment surface making up at least a portion of the second side of the body.

5. The guide of claim 4 or system of claim 1, wherein at least a portion of the guide surface is substantially convex.

6. The guide of claim 4 or system of claim 1, wherein the opposing side wall includes a substantially concave portion.

7. The guide of claim 4 or system of claim 1, wherein the opposing side wall includes a substantially concave portion and wherein the concave portion is positioned substantially opposite the spring-fit structure.

8. The guide of claim 4 or system of claim 1, wherein the spring-fit structure is positioned adjacent to the entrance opening.

9. The guide of claim 4 or system of claim 1, wherein the body, the guide slot, and the spring-fit structure comprise a single, unitary structure.

10. The guide of claim 4 or system of claim 1, wherein the at least a portion of the cutting-plane side wall located within the cutting plane and the spring-fit structure are formed of a polymer material.

11. The guide of claim 4 or system of claim 1, wherein the surgical instrument comprises an instrument selected from the group consisting of a saw, a drill, and a pin.

12. The guide of claim 4 or system of claim 1, wherein the position and/or orientation of the predetermined cutting plane relative to the body is based, at least in part, on patient-specific information.

13. A guide for a surgical instrument for use in treating a joint of a patient, the guide comprising:
   a body having a guide slot extending through at least a portion of the body from a first side of the body to a second side of the body,
   wherein the guide slot is dimensioned to receive the surgical instrument through an entrance opening and guide the surgical instrument along a path extending from an exit opening in a direction substantially opposite the entrance opening and substantially along a predetermined cutting plane,
   wherein the entrance opening is located on the first side of the body and the exit opening is located on the second side of the body,
   wherein a cutting-plane side wall of the guide slot includes at least a portion substantially located within the cutting plane, and
   wherein an opposing side wall of the guide slot is positioned substantially opposite the cutting-plane side wall and includes at least one spring-fit structure, the at least one spring-fit structure comprising:
      a guide surface substantially facing the cutting-plane side wall; and
      a flexing portion connected to the body and supporting at least a portion of the guide surface, the flexing portion configured to allow at least a portion of the guide surface to move in a direction substantially away from the cutting plane when the surgical instrument is inserted into the guide slot and contacts at least a portion of the guide surface,
   wherein the body further comprises at least one alignment surface having at least a portion with a shape based, at least in part, on patient-specific information regarding a surface of the patient's joint such that the guide can be positioned against and aligned with the corresponding surface of the patient's joint in a predetermined position and/or orientation, and
   wherein the exit opening is located within the alignment surface, the alignment surface making up at least a portion of the second side of the body.

* * * * *